US00PP22338P2

(12) United States Plant Patent
Jacobs

(10) Patent No.: US PP22,338 P2
(45) Date of Patent: Dec. 13, 2011

(54) *ALSTROEMERIA* PLANT NAMED 'ZAPRIELIA'

(50) Latin Name: *Alstroemeria hybrida*
Varietal Denomination: Zaprielia

(75) Inventor: Henricus Cornelius Maria Jacobs, Rijsenhout (NL)

(73) Assignee: van Zanten Plants b.v., Hillegom (NL)

( * ) Notice: Subject to any disclaimer, the term of this patent is extended or adjusted under 35 U.S.C. 154(b) by 0 days.

(21) Appl. No.: 12/925,454

(22) Filed: Oct. 21, 2010

(51) Int. Cl.
*A01H 5/00* (2006.01)

(52) U.S. Cl. ..... Plt./309

(58) Field of Classification Search ..... Plt./309
See application file for complete search history.

*Primary Examiner* — Kent L Bell
(74) *Attorney, Agent, or Firm* — C. A. Whealy

(57) ABSTRACT

A new and distinct cultivar of *Alstroemeria* plant named 'Zaprielia', characterized by its compact, upright, somewhat outwardly spreading and mounded plant habit; vigorous growth habit; dark pink-colored flowers; and good container and garden performance.

1 Drawing Sheet

Botanical designation: *Alstroemeria hybrida.*
Cultivar denomination: 'ZAPRIELIA'.

BACKGROUND OF THE INVENTION

The present invention relates to a new and distinct cultivar of *Alstroemeria* plant, botanically known as *Alstroemeria hybrida,* commercially used as a garden-type *Alstroemeria* plant, and hereinafter referred to by the name 'Zaprielia'.

The new *Alstroemeria* plant is a product of a planned breeding program conducted by the Inventor in Rijsenhout, The Netherlands. The objective of the breeding program is to create new garden-type *Alstroemeria* cultivars with uniform plant habit, freely flowering habit, attractive foliage and flower coloration and excellent garden performance.

The new *Alstroemeria* plant originated from a cross-pollination made by the Inventor in Rijsenhout, The Netherlands in May, 2006, of a proprietary *Alstroemeria hybrida* selection identified as code number 04-1060-001, not patented, as the female, or seed, parent with a proprietary *Alstroemeria hybrida* selection identified as code number 05-6213-001, not patented, as the male, or pollen, parent. The new *Alstroemeria* plant was discovered and selected by the Inventor as a single flowering plant from within the progeny of the stated cross-pollination in a controlled greenhouse environment in Rijsenhout, The Netherlands in June, 2007.

Asexual reproduction of the new *Alstroemeria* plant by rhizome divisions in a controlled greenhouse environment in Rijsenhout, The Netherlands since August, 2007, has shown that the unique features of this new *Alstroemeria* plant are stable and reproduced true to type in successive generations.

SUMMARY OF THE INVENTION

Plants of the new *Alstroemeria* have not been observed under all possible environmental conditions. The phenotype may vary somewhat with variations in environment and cultural practices such as temperature and light intensity without, however, any variance in genotype.

The following traits have been repeatedly observed and are determined to be the unique characteristics of 'Zaprielia'.

These characteristics in combination distinguish 'Zaprielia' as a new and distinct cultivar of *Alstroemeria:*

1. Compact, upright, somewhat outwardly spreading and mounded plant habit.
2. Vigorous growth habit.
3. Dark pink-colored flowers.
4. Good container and garden performance.

Plants of the new *Alstroemeria* differ primarily from plants of the female parent selection in flower color as plants of the female parent selection have lighter pink-colored flowers. In addition, plants of the new *Alstroemeria* have larger flowers than plants of the female parent selection.

Plants of the new *Alstroemeria* differ primarily from plants of the male parent selection in flower color as plants of the male parent selection have orange-colored flowers. In addition, plants of the new *Alstroemeria* are more compact than plants of the male parent selection.

Plants of the new *Alstroemeria* can be compared to plants of *Alstroemeria hybrida* 'Staprilene', disclosed in U.S. Plant Pat. No. 11,683. In side-by-side comparisons conducted in Rijsenhout, The Netherlands, plants of the new *Alstroemeria* differed primarily from plants of 'Staprilene' in the following characteristics:

1. Plants of the new *Alstroemeria* were not as broad as plants of 'Staprilene'.
2. Plants of the new *Alstroemeria* had shorter lateral branches than plants of 'Staprilene'.
3. Plants of the new *Alstroemeria* had smaller flowers than plants of 'Staprilene'.
4. Plants of the new *Alstroemeria* and 'Staprilene' differed in flower color.

BRIEF DESCRIPTION OF THE PHOTOGRAPH

The accompanying colored photograph illustrates the overall appearance of the new *Alstroemeria* plant showing the colors as true as it is reasonably possible to obtain in colored reproductions of this type. Colors in the photograph may differ slightly from the color values cited in the detailed botanical description which accurately describe the colors of the new *Alstroemeria* plant. The photograph comprises a side perspective view of a typical flowering plant of 'Zaprielia' grown in a container.

DETAILED BOTANICAL DESCRIPTION

The aforementioned photograph and following observations and measurements describe plants of the new *Alstroemeria* grown during the late summer in 14-cm containers in a glass-covered greenhouse in Rijsenhout, The Netherlands. During the production of the plants, day temperatures ranged from 15° C. to 25° C. and night temperatures ranged from 10° C. to 15° C. Plants were six months old when the photograph and the description were taken. In the following description, color references are made to The Royal Horticultural Society Colour Chart, 1966 Edition, except where general terms of ordinary dictionary significance are used.

Botanical classification: *Alstroemeria hybrida* 'Zaprielia'.

Parentage:

*Female, or seed, parent.*—Proprietary *Alstroemeria hybrida* selection identified as code number 04-1060-001, not patented.

*Male or pollen parent.*—Proprietary *Alstroemeria hybrida* selection identified as code number 05-6213-001, not patented.

Propagation:

*Type.*—In vitro rhizogenesis.

*Time to produce a rooted young plant, summer.*—About 40 days.

*Time to produce a rooted young plant, winter.*—About 60 days.

*Root description.*—Fibrous, fleshy, thick; close to 155D in color.

*Rooting habit.*—Freely branching; moderately dense.

*Rhizomes.*—Shape: Elongate; rounded. Length: About 10 cm to 30 cm. Diameter: About 3 mm to 10 mm. Texture: Smooth. Color: Close to 155D.

Plant description:

*Plant and growth habit.*—Compact, upright, somewhat outwardly spreading and mounding plant habit; freely branching habit, bushy appearance; vigorous growth habit.

*Plant height.*—About 20 cm to 26 cm.

*Plant diameter (spread).*—About 25 cm to 35 cm.

Lateral branch description:

*Aspect.*—Mostly upright.

*Length.*—About 7 cm to 9 cm.

*Diameter.*—About 2 mm to 3 mm.

*Internode length.*—About 3 mm to 10 mm.

*Strength.*—Strong.

*Texture.*—Smooth, glabrous.

*Color.*—Close to 145C.

Foliage description:

*Appearance.*—Leaves asymmetrical; sessile.

*Length.*—About 7.3 cm to 9.2 cm.

*Width.*—About 1.7 cm to 2.6 cm.

*Shape.*—Lanceolate.

*Apex.*—Acute.

*Base.*—Cuneate.

*Margin.*—Entire; slightly undulate.

*Texture, upper and lower surfaces.*—Smooth, glabrous.

*Venation pattern.*—Parallel.

*Color.*—Developing and fully expanded leaves, upper surface: Close to 147A; venation, close to 141D. Developing and fully expanded leaves, lower surface: Close to 147B; venation, close to 137D.

Flower description:

*Flower type and habit.*—Single cup-shaped flowers arranged in compound umbels; flowers face mostly outwardly; perianth segments separate; freely flowering habit with potentially 25 flowers per inflorescence.

*Natural flowering season.*—Flowering continuous during the spring in The Netherlands; plants begin flowering about 80 to 90 days after planting.

*Fragrance.*—None detected.

*Flower longevity on the plant.*—About four weeks; flowers not persistent.

*Flower buds.*—Length: About 4.3 cm to 4.5 cm. Diameter: About 1.3 cm to 1.5 cm. Shape: Roughly ovoid. Color: Close to 185A.

*Umbel height.*—About 7 cm to 9 cm.

*Umbel diameter.*—About 11 cm to 12 cm.

*Flower diameter.*—About 5.5 cm.

*Flower depth.*—About 6.5 cm.

*Perianth.*—Arrangement: Six arranged in two whorls, each whorl with two lateral and one median segments. Inner perianth, lateral segments: Length: About 5.4 cm to 6.2 cm. Width: About 1.8 cm to 2.1 cm. Shape: Oblanceolate. Apex: Wishbone-shaped. Base: Attenuate. Margin: Entire; slightly undulate. Texture, upper and lower surfaces: Smooth, glabrous. Color, when opening and fully opened, upper surface: Close to 54A; center, close to 34C; towards the base, close to 15A; stripes, close to 183A. Color, when opening and fully opened, lower surface: Close to 54A; center, close to 34C; towards the base, close to 15A. Inner perianth, median segment: Length: About 5 cm to 5.5 cm. Width: About 1.9 cm to 2.1 cm. Shape: Oblanceolate. Apex: Wishbone. Base: Attenuate. Margin: Entire; weakly undulate. Texture, upper and lower surfaces: Smooth, glabrous. Color, when opening and fully opened, upper surface: Close to 54A; stripes, close to 183A. Color, when opening and fully opened, lower surface: Close to 54A. Outer perianth, lateral segments: Length: About 5.4 cm to 5.8 cm. Width: About 3 cm to 3.6 cm. Shape: Obovate. Apex: Embedded pointed. Base: Attenuate. Margin: Entire; slightly undulate. Texture, upper and lower surfaces: Smooth, glabrous. Color, when opening and fully opened, upper surface: Close to 54A. Color, when opening and fully opened, lower surface: Close to 54A. Outer perianth, median segment: Length: About 5.2 cm to 5.7 cm. Width: About 3 cm to 3.5 cm. Shape: Obovate. Apex: Embedded pointed. Base: Attenuate. Margin: Entire; slightly undulate. Texture, upper and lower surfaces: Smooth, glabrous. Color, when opening and fully opened, upper surface: Close to 54A. Color, when opening and fully opened, lower surface: Close to 54A.

*Pedicels.*—Length: About 2 mm to 15 mm. Diameter: About 2 mm to 3 mm. Strength: Strong. Angle: About 20° to about 30° from vertical. Texture: Smooth, glabrous. Color: Close to 138B.

*Reproductive organs.*—Stamens: Quantity per flower: Six. Anther shape: Elliptical. Anther length: About 5 mm to 6 mm. Anther diameter: About 2 mm. Anther color: Close to 176B. Pollen amount: Scarce. Pollen color: Close to 165B. Pistils: Quantity per flower:

One. Style length: About 3.4 cm to 3.7 cm. Style color: Close to 41B. Stigma shape: Three-parted. Stigma color: Close to 41C. Ovary color: Close to 143C.

*Fruit/seed.*—Fruit and seed development have not been observed.

Disease/pest resistance: Plants of the new *Alstroemeria* have not been observed to be resistant to pathogens and pests common to *Alstroemeria.*

Garden performance: Plants of the new *Alstroemeria* have been observed to have good garden performance and to tolerate wind, rain and temperatures from about −5° C. to about 40° C.

It is claimed:

1. A new and distinct *Alstroemeria* plant named 'Zaprielia' as illustrated and described.

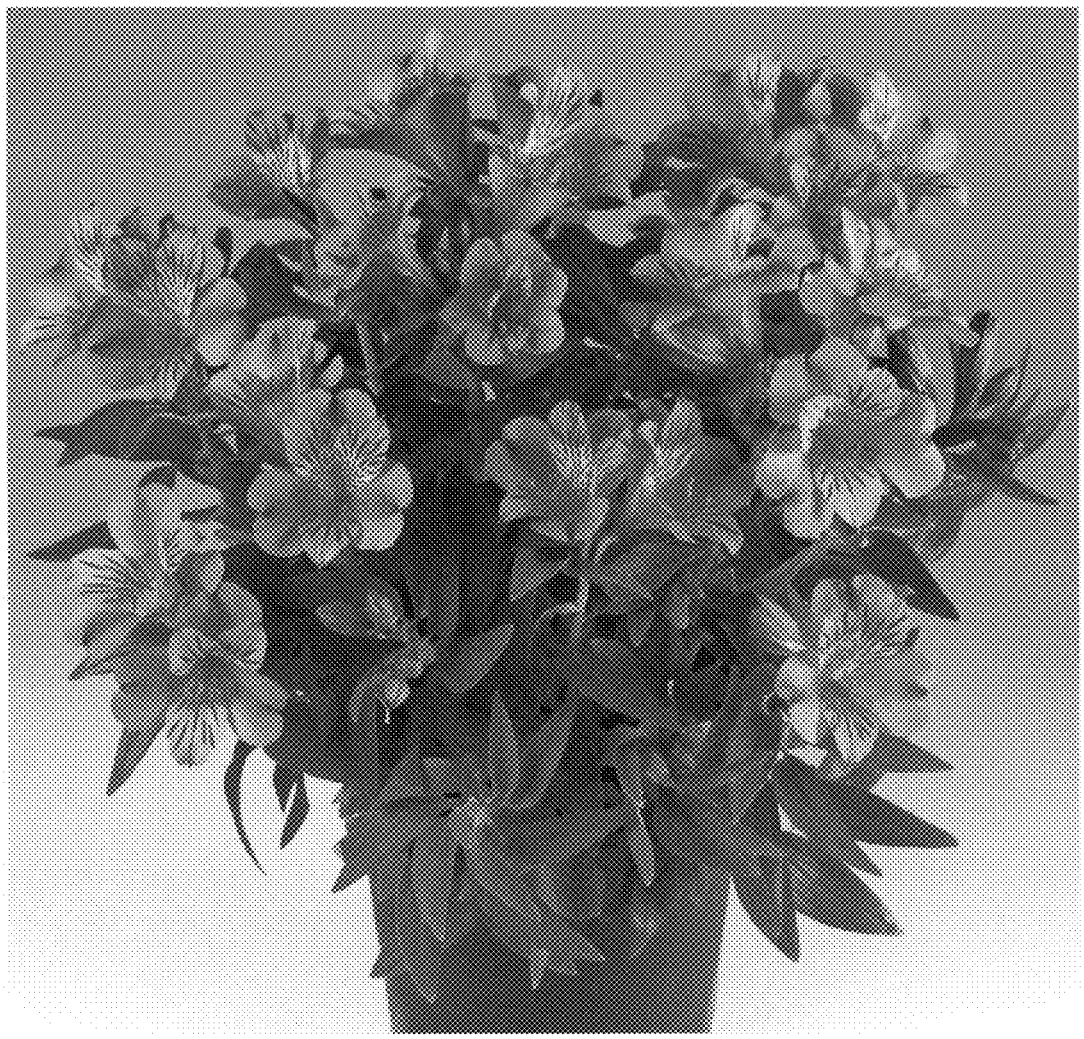

* * * * *